United States Patent [19]

Lobdell

[11] Patent Number: 5,255,556
[45] Date of Patent: Oct. 26, 1993

[54] AIR QUALITY INDICATOR AND CONTROL FOR AIR QUALITY MACHINE

[75] Inventor: Vincent G. Lobdell, Pulaski, N.Y.

[73] Assignee: Tec-Way Air Quality Products, Inc., East Syracuse, N.Y.

[21] Appl. No.: 775,570

[22] Filed: Oct. 15, 1991

[51] Int. Cl.$^5$ ............................................. G01W 1/04
[52] U.S. Cl. .............................. 73/31.02; 73/863.21; 340/602
[58] Field of Search ................. 73/23.2, 31.02, 863.21, 73/864.33; 340/601, 602, 627

[56] References Cited

U.S. PATENT DOCUMENTS

| | | | |
|---|---|---|---|
| 3,976,450 | 8/1976 | Marcote et al. | 73/31.02 X |
| 4,173,886 | 11/1979 | Archbold et al. | 73/31.02 |
| 4,324,146 | 4/1982 | Born | 73/863.21 X |
| 4,786,472 | 11/1988 | McConnell et al. | 73/31.02 X |
| 4,868,546 | 9/1989 | Dumbeck | 73/31.02 X |
| 4,909,090 | 3/1990 | McGown et al. | 73/863.12 X |
| 5,088,314 | 2/1992 | Takahsi | 73/31.02 X |
| 5,138,889 | 8/1992 | Conrad | 73/863.12 |

FOREIGN PATENT DOCUMENTS 2088055  6/1982  United Kingdom ............. 73/864.33

*Primary Examiner*—Hezron E. Williams
*Assistant Examiner*—Joseph W. Roskos
*Attorney, Agent, or Firm*—Wall and Roehrig

[57] ABSTRACT

A portable air quality indication unit senses and indicates at least the ambient concentration of aerosols and particulates, the ambient concentration of a gas such as CO, the ambient temperature and the relative humidity, and displays the same. The gas concentration level and particulates concentration level are provided as good or satisfactory, bad or unsatisfactory, or fair/good, i.e., marginal depending on the relation of the detected level to the predetermined threshold level values of gas concentration, and particulates concentration. Temperature and relative humidity can be displayed on liquid crystal displays. A microprocessor circuit within the unit assumes a low-power standby mode, in which the gas and particulates sensor means are sampled at a relatively low rate, when the particulates level and gas concentration level are below their respective TLVs. However, when an abnormal level is detected, the microprocessor circuit assumes a high-sensitivity mode in which the gas sensors are sampled at a relatively high rate.

7 Claims, 3 Drawing Sheets

AIR QUALITY INDICATOR AND CONTROL FOR AIR QUALITY MACHINE

BACKGROUND OF THE INVENTION

This invention relates to the real-time monitoring and control of air quality in a work or living space, and is more particularly concerned with devices that provide a measurement of health quality and contaminant concentration levels of ambient air. The invention is also concerned with control devices for controlling operation of air treatment and removal of particulates in connection with a room air health and comfort unit.

In order to provide satisfactory air quality in an environmental work space or living space, it is desirable to obtain an indication of the contaminant concentrations in the space, both in terms of gas or vapor concentrations (i.e., CO, $SO_2$ or other noxious gases), or airborne particulate concentrations, (i.e., dust, aerosol droplets, bacteria, spores, pollen, and viruses). Then it is necessary to compare the measured values with threshold limit values (TLVs) which correspond to the levels of contaminant concentration to which humans can be continuously exposed without significant adverse health risk. Levels higher than TLVs represent air quality that is marginal to unacceptable.

In the United States, threshold limit values are established by government agencies such as the National Institute of Occupational Safety and Health (NIOSH) and the Occupational Safety and Health Agency (OSHA) based on information compiled by the American Conference of Governmental and Industrial Hygienists (ACGIH) with additional published data from the Environmental Protection Agency (EPA), and standards from the American Society of Heating, Refrigeration and Air Conditioning Engineers.(ASHRAE)

However, measurement of air quality has required special, complex equipment to be used by specially trained personnel. It was not possible for a lay person to obtain a real-time reading of air quality in an environmental work or living space. In addition, there has not been any suitable combined control circuitry available for controlling room air quality equipment, for controlling comfort factors, such as heat and relative humidity, as well as health factors such as particulate and gas concentrations to remain below their respective TLVs. There has been no control circuit provided for environment control equipment to monitor and control air quality based on temperature, relative humidity, particulates and aerosols concentration or gas concentration levels.

OBJECTS AND SUMMARY OF THE INVENTION

Accordingly, it is an object of this invention to provide accurate real-time sensing and display of environmental air quality (VIA indication of humidity, temperature, and contaminant level).

It is another object to provide an environmental air quality measuring device which can monitor air quality parameters and display same in real time.

It is a further object to provide control of a room air health and comfort unit to maintain temperature and relative humidity within desired limits and to maintain particulate and gas concentrations below predetermined TLVs.

According to an aspect of this invention a portable electronic monitoring device senses and indicates air quality within a given space. Within its housing the device has a particulate sensor for detecting the ambient concentration of aerosols and particulates in the space and for comparing the detected level with a predetermined particulates TLV. A gas sensor in the housing detects the ambient concentration level of one or more predetermined gases, such as CO, $CH_4$, $SO_2$, etc., and compares the same with a predetermined gas TLV. A temperature sensor measures the ambient temperature in the environmental space; a humidity sensor in the housing detects ambient relative humidity in the environmental air in the vicinity of the device. There is a particulate display on a panel of the housing, and the display can be in the form of a row of LEDs with one LED indicating a satisfactory air quality when the detected particulate level is within the acceptable TLV based upon established standards. A similar row of LEDs or equivalent display indicates acceptable gas concentration when the target gas or gases have a concentration below the gas TLV. When the gas or particulate level is detected above the TLV another LED illuminates to indicate that the air quality has become marginal or unacceptable. There are also displays, such as liquid crystal displays, to indicate the temperature and relative humidity of the air in the vicinity of the device. These can be separate or a combined dual-function display. The control circuit for sampling the various sensors and actuating the displays assumes a low power standby mode when the sensors indicate that the particulate and gas concentrations are below the respective TLVs, and the humidity and temperature are within their target comfort ranges. If any of these detected parameters rises (or falls) to an abnormal level, e.g. if the particulate concentration level reads higher than the particulate TLV, then the control circuit automatically switches over to a high sensitivity mode. In the low sensitivity mode the control circuit samples the sensors at a low rate; this conserves battery power and also limits false readings of excessive gas or particulate concentration. When the control circuit switches to the high sensitivity mode, the sensors are sampled more frequently. However, in this mode a repetition of high readings for three or more samples is required to produce an "unacceptable" display on the gas or particulate concentration display. Also three or more successive high readings of gas or particulate are required for the control circuit to actuate an alarm. The alarm can be a flashing LED if the gas or particulate concentration is just above the TLV (indicating marginal air quality) or a sounder or buzzer if the gas or particulate concentration is well above the TLV (indicating potentially health-threatening air quality).

The device can be portable or placed in a permanent location in a room where air quality should be monitored. Because of the low power requirements, the device can be left on continuously.

The same control circuit can also be employed to control a room air health and comfort air quality machine which can provide air purification (both of particulates and of one or more gases), temperature control (heating, cooling or both), and humidity control (humidification or dehumidification). The unit housing has an air inlet to admit room air into an air pathway. The air passes through mechanical prefilter media for collection of larger airborne contaminants, then through an ionization section and electrostatic charged grid, mesh, or media for removal of microscopic particulates from the air stream. Organic compounds are removed from the air stream through the use of radiant energy sources, and/or adsorptive, absorptive or catalytic media filters, such as activated carbon, silica gel, or alumina to remove gaseous contaminants such as $SO_2$, $CO_2$, $O_3$ and/or other gases. Each of the aforementioned filter systems can be used independently or in any combination in the machine. A blower then moves the air past heat control elements, e.g. an evaporator heat exchange coil to cool and dehumidify the air and/or a heating coil to heat the air, as required. After this a humidifier, either a web of porous mesh or other material in contact with water in a reservoir, or an ultrasonic humidification process can be actuated to add water vapor to the air stream as required. In a favorable embodiment, the unit is free-standing and can be wheeled into a room where air comfort and quality needs to be controlled closely. However, in other embodiments it can be a permanent installation serving a room or suite of rooms.

As in the measuring unit discussed previously, in this embodiment there are temperature and humidity sensors plus particulate and gas sensors. There are also temperature and humidity setpoint selectors, and particulate and gas concentration displays. These are preferably each a series of LEDs disposed on a front panel of the unit. The control circuit operates the blower or fan, heater, air conditioner compressor, humidifier, and dehumidifier, as required, based on outputs of the temperature and humidity sensors as compared with high and low temperature setpoints and a relative humidity setpoint. The blower speed can be increased when the particulate concentration is high.

The control circuit assumes a low-sensitivity mode when the sensors all indicate normal levels of the measured parameters, and if the particulate or gas concentration or the temperature reaches an abnormal level (i.e., below a heating setpoint or above an air conditioning setpoint), the control circuit automatically switches over to a high-sensitivity mode, as described before in connection with the monitoring device.

Pressure differential can also be detected, and if this becomes abnormal, an indicator will signal that various system filters should be changed or cleaned.

The above and many other objects, features, and advantages of this invention will present themselves to those skilled in the art from the ensuing description of selected preferred embodiments, to be read in conjunction with the accompanying Drawing.

DETAILED DESCRIPTION OF A PREFERRED EMBODIMENT

The pathway of air through an air health and comfort unit should have elements to perform the various air handling, purification and treatment functions, for example, as follows:

1. Mechanical pre-filter media devices to filter the larger air contaminants out of the air stream.

2. Ionizing section with high voltage section to ionize the gas molecules in the air stream thus producing charges which attach themselves to air contaminants.

3. Collecting section, i.e. high voltage alternately-charged section of grid mesh or media to collect the microscopic airborne contaminants.

4. Radiant energy section, e.g., high-and low-frequency radiant energy sources to remove airborne organic compounds.

5. After-filter section where chemisorb media filters utilize adsorption, absorption or catalytic means to remove volatile organic compounds from the air stream.

6. Humidification section, designed to add water vapor, as needed, to the air stream.

7. Air handler system for drawing air into the unit and exhausting it back into the room environment.

8. Heater section designed to add or heat energy as needed to the air stream.

9. Cooling section designed to cool the air stream, as needed.

10. Dehumidification section designed to remove water vapor from the air stream, as necessary.

Figure 2:
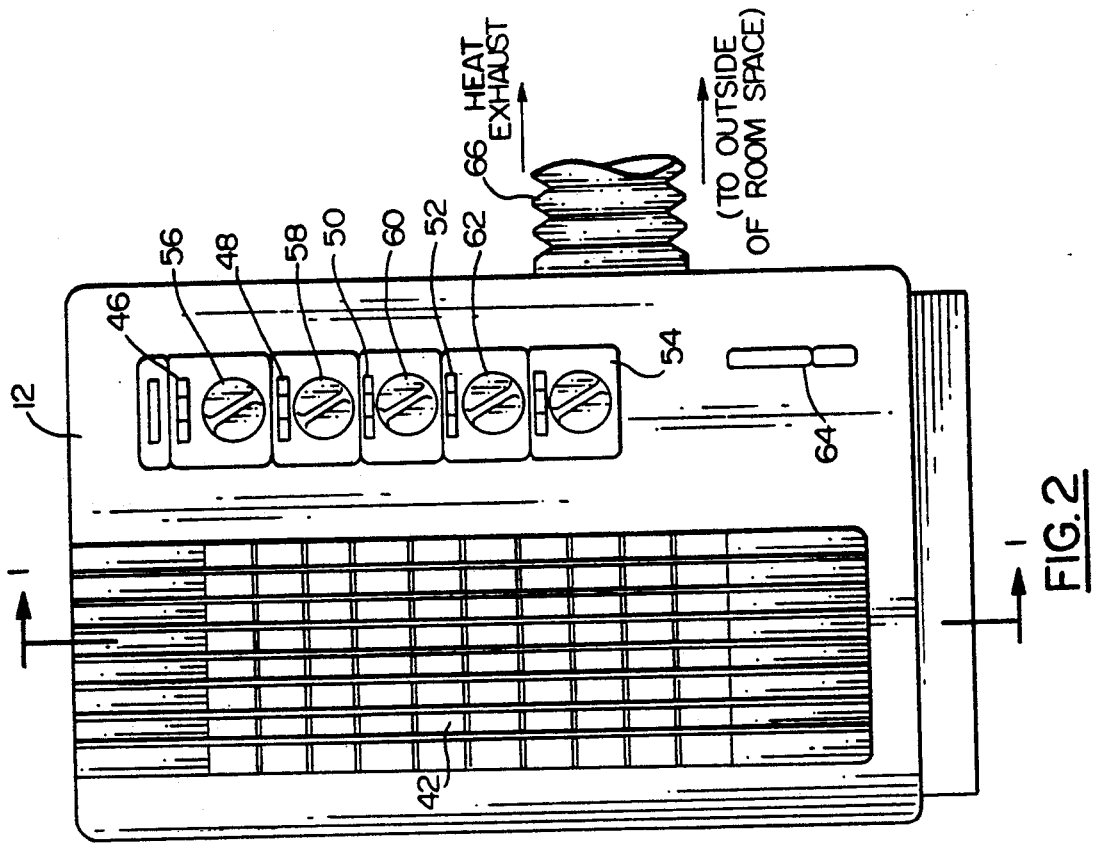
FIG. 2 is a front elevation of the unit of FIG. 1, showing at 1—1 the viewing direction of FIG. 1.
Figure 1:
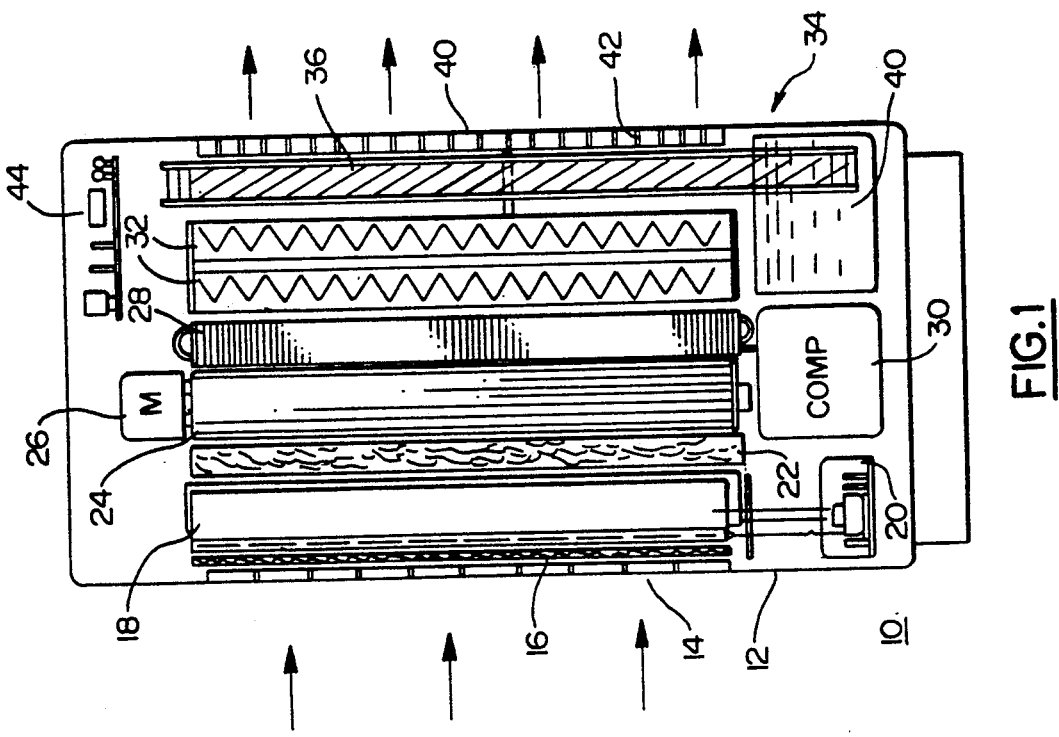
FIG. 1 is a sectional side elevation of a room air health and comfort machine according to one preferred embodiment of this invention.

With reference to the Drawing, and initially to FIGS. 1 and 2, a free-standing air conditioning and air purification unit 10 has a shell or housing 12. Intake air from the room, work space, or living space, passes into the unit through a back grill 14 and thence through a coarse filter or prefilter 16 into an electrostatic air purifier 18. Preferably, the air purifier 18 is of the charged-grid type, to which high voltage is supplied from a power supply 20. Air proceeds along its pathway through the unit 10 passing through a gas-adsorptive filter 22. This filter 22 employs active carbon, silica gel, or another adsorptive or absorptive medium. A blower 24 positioned after the filter 22 moves the air through the unit 10. Here, the blower 24 is of the cross-flow type having a vertical axis and a motor 26 at one end. In other embodiments, one or more propeller fans could be used instead. The blower 24 forces air through a cooling coil 28, for example, an evaporator coil of an air conditioning system, of which a compressor 30 is shown. A condenser coil would also be associated with the cooling coil 28 and compressor 30, but is not shown in this drawing.

A set of heater coils 32 is positioned after the cooling coil 28. Preferably, these are electric coils of a high-efficiency resistive heating design. A humidifier 34 follows the heater coils 32, and can be formed of a continuous web 36 of a rather porous mesh which when actuated, travels between a water reservoir 40 and air in the pathway, which passes from there through a front grill 42, where the conditioned air is discharged back into the room. A separate reservoir 40 can also be employed for catching condensed water from the cooling coil 28 when the unit 10 is in a cooling mode. A control circuit 44, here shown in FIG. 1, controls the operation of the various parts of this unit 10, in accordance with ambient conditions, as compared to predetermined or selected setpoints.

As shown in FIG. 2, there are various control knobs and indicators on a front panel of the housing 12. These are coupled to the control circuit 44. There is a bar-type LED particulates concentration indicator 46 and a similar LED gas concentration indicator 48, and there are also a digital display of relative humidity 50 and a digital display of ambient temperature 52. Both of these are preferably liquid crystal displays, but other visual display means could be employed. In other embodiments a single display can show humidity and temperature alternately.

An on/off, high/low fan speed switch 54 is provided on the front of the unit 10, as are setpoint adjustments including an adjustment knob 56 for particulates concentration sensitivity, a knob 58 for gas concentration sensitivity, a knob 60 for adjusting the relative humidity setpoint, and another knob 62 for adjusting the temperature setpoint or setpoints. On the lower part of the front of the housing there is a visible water reservoir level indicator 64 to indicate the amount of water contained in the reservoir 40. Also shown in FIG. 2 is an exhaust air conduit 66, for conducting out of the room another stream of air which passes over the not-shown condenser coil to conduct heat to outside of the living space or workspace.

In this embodiment, the control circuit 44 includes a digital control containing a microprogram which controls the speed of the blower 24 as a function of particulates concentration or gas concentration level. That is, the blower speed increases if the detected level is higher than a predetermined threshold level value (TLV). Other functions are also possible to be controlled by microprogramming, i.e., for controlling the operation of the compressor 30, the heater coils 32, or the humidifier 34 as a function of temperature and relative humidity. Such programs are well known.

Figure 3:
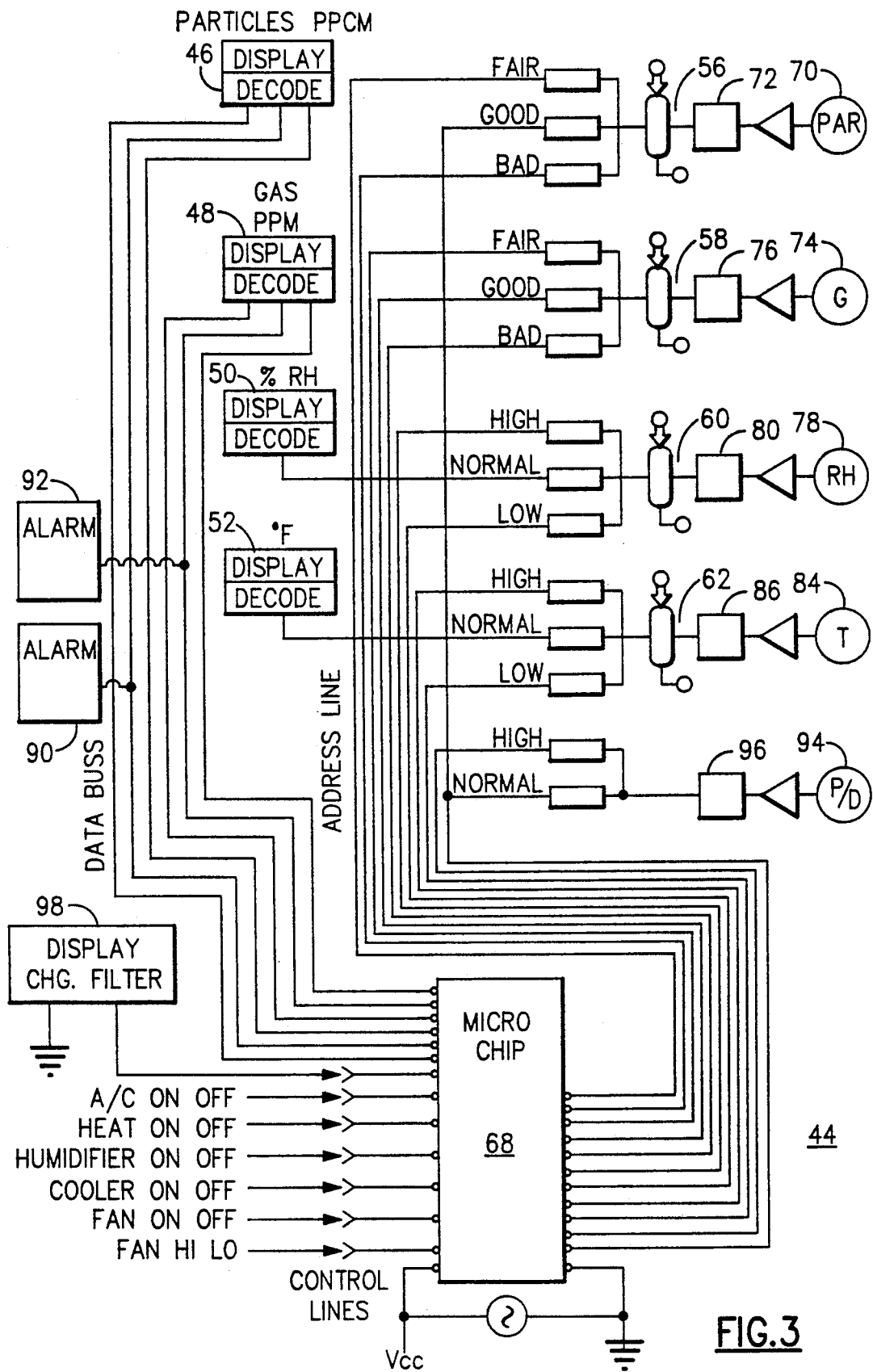
FIG. 3 is a schematic view of the sensors, displays, and control circuitry of this invention.

FIG. 3 is a schematic circuit diagram of one form of the control circuit 44 according to this invention. Here are shown the particulates concentration level setpoint selector 46, the gas concentration setpoint selector 48, relative humidity setpoint selector 50, and temperature setpoint selector 52. At the heart of the circuit 44 is a microprocessor integrated circuit chip 68 with a number of inputs (shown on the right hand side) as well as outputs (on the left hand side) used to control heat, air conditioning, humidity, and fan speed, and to actuate a number of displays.

A particulate sensor 70 senses the concentration of particulates in the ambient air in the vicinity of the unit 10, and supplies a particulate level signal to a comparator 72 which compares that level with a setpoint provided from the selector 46. In this case, the comparator provides a number of outputs, for example, indicating "good" or acceptable air quality when the detected particulates level is below the established TLV, a "bad" or unacceptable signal when the particulates level is above the particulate TLV, and one or more marginal or "fair" signals when the particulate level is near the TLV.

A gas sensor 74 detects the level of concentration of one or more undesirable gases in the ambient air. These gases, for example, could include carbon monoxide, sulfur dioxide, methane, or other toxic or health-threatening vapors. The gas sensor 74 provides an output level which is fed to a comparator 76. This comparator is also provided with a setpoint from the setpoint selector 58, and thus provides a "good" indication, an "unacceptable" indication, and one or more intermediate indications, depending on the value of the detected gas concentration relative to the gas TLV.

A relative humidity sensor 78 provides a relative humidity level to a comparator 80 which is also coupled to the relative humidity setpoint selector 60. The relative humidity level is also fed to the relative humidity display where it is decoded and displayed in digital form.

A temperature sensor 84 senses the temperature of the air in the vicinity of the unit 10, and supplies a temperature value to a comparator 86 which is also coupled to the temperature setpoint selector 60. The temperature value is also fed to the temperature display 52, where it is decoded and displayed in digital form.

An alarm 90, which can be an audible or visible alarm, is actuated if the particulate concentration is detected to be at an unacceptable level.

There is also a pressure differential detector 94 disposed along the pathway of air within the unit 10, for sensing pressure differential, for example, across the gas absorbent filter 22. A pressure differential signal is fed from the detector 94 to a comparator 96 which provides a signal along a high channel or "normal" channel depending on the value of the pressure differential.

If the pressure is too high, the microprocessor chip 68 will light a change-filter display 98, to indicate that the gas filter 22 should be changed out.

One set of outputs from the microprocessor chip 68 supplies inputs of the particulates LED indicator 46 which, as aforementioned, includes an LED indicator which lights if the particulates level is satisfactory, and one or more additional LED indicators which light when the particulates level is less than satisfactory. This indicator 46 can also include the visual or audible alarm 90 which is actuated when the particulates sensor 70 detects that the particulates level is well above the particulates TLV.

In similar fashion, a number of the outputs of the microprocessor chip 68 are connected to inputs of the gas sensor display or indicator 48, in which include an LED indicator which lights when the detected gas concentration level is below the gas TLV, as well as one or more additional LED indicators which light when the gas level is at an unsatisfactory or unsafe level, that is, near or below the gas TLV. Also, the audible or visual alarm can be actuated when the gas sensor 74 detects that the gas in question has a concentration above the appropriate L.E.L. or TLV.

The microprocessor chip 68 is suitably programmed to assume a low-sensitivity active mode, i.e. a standby mode, when the detected temperature and humidity are within normal bounds, that is, if the humidity is above a "dry" level, such as 45% R.H., and if the temperature is above the temperature for which heat is required yet below the temperature for which cooling is required, and also where the particulate and gas concentrations are below the respective threshold limit values. In other cases, the microprocessor chip 68 is operative to switch over to a high sensitivity mode, that is, when either heating or cooling is called for, or if moisture must be added to bring the relative humidity up to an acceptable level. The microprocessor chip 68 also automatically switches over to a high sensitivity mode when the detected particulate concentration is above the particulate TLV or when the gas concentration is above the gas TLV. If all of these levels, to wit, temperature, relative humidity, gas concentration and particulate concentration are returned to a normal level, the chip 68 remains in the high-sensitivity mode for a predetermined interval, and then returns to the low-sensitivity mode. On the other hand, to prevent spurious or intermittent signals from actuating the circuit 44, a predetermined number of consecutive time samples of particulate level, gas level, relative humidity, and/or temperature, are required to be abnormal before the high-sensitivity mode is selected.

When in the low-sensitivity mode, the microprocessor chip 68 is operative to sample its respective inputs of particulate, gas, relative humidity, and temperature at a relatively low rate. However, in the high-sensitivity mode, the chip 68 is operative to sample the particulate level, the gas level, the temperature level, and the relative humidity level at relatively high rate. The blower speed can then be automatically increased if additional particulate removal or gas removal is called for. If heating or cooling is called for, the microchip 68 is operative to automatically actuate the compressor 30 or the heater coils 32, as appropriate. If the humidity level is detected to be too low, the humidifier 34 is automatically actuated. Thus, the air conditioning and air purification unit 10 automatically controls the air quality in the workspace or living space to provide a healthy and comfortable work and living environment, and at the same time indicates the comfort level, as well as the healthiness of the air, in terms of particulate level, gas concentration level, temperature, and relative humidity.

Figure 4:
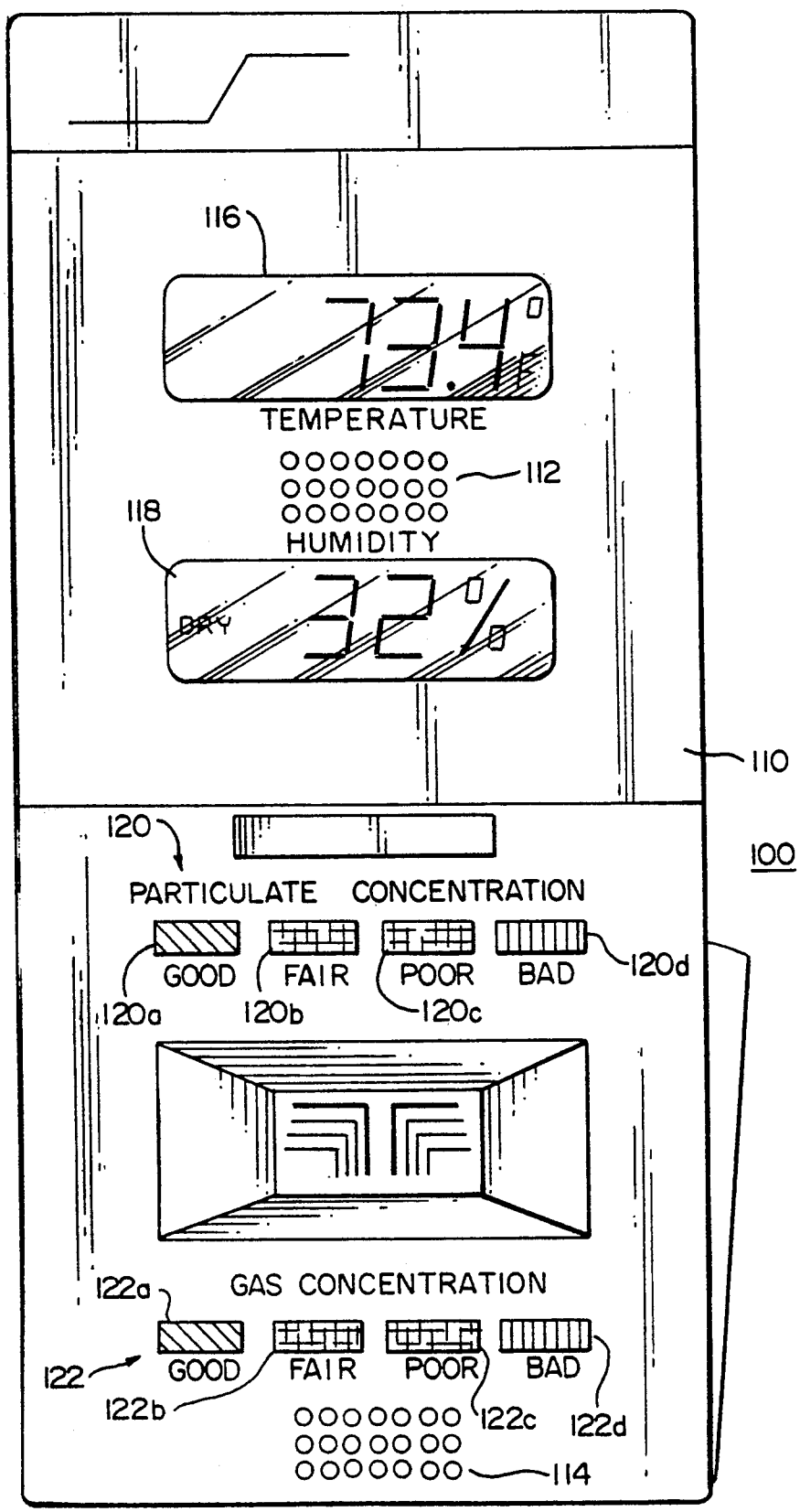
FIG. 4 is a top plan view of a hand-held monitoring unit according to another embodiment of this invention.

As shown in FIG. 4, an air quality indicator 100 is provided as a hand-held or wall-mounted instrument for measuring and indicating the elements of air quality which have been described in connection with the embodiment of FIG. 1. Here there is a housing or shell 110 with openings 112 to admit air to relative humidity and temperature sensor within the instrument, as well as further openings 114 to admit air in the vicinity of the instrument to a particulate sensor and a gas sensor. On the front of the instrument there are provided an LCD temperature display 116, and a LCD relative humidity display 118. The temperature can be provided in degrees F. or degrees C., while relative humidity is provided, as is conventional, in percent.

An LED particulate concentration indicator 120 is provided as a bar-type indicator having a green LED 120a which lights when the particulates level is below the particulate TLV, two yellow LEDs 120b and 120c which light when the detected particulate level is between the high and low particulate TLV, thus indicating fair or poor air quality, and a red LED 120d which lights when the detected particulate concentration is above the TLV, thus indicating an unacceptable or dangerous particulate concentration.

A second LED indicator 122 is employed for indicating the concentration of a gas or vapor, such as carbon monoxide. Here, as in the particulates indicator, this indicator 122 has a green LED 122a which lights when the gas concentration is below the gas TLV, first and second yellow LEDs 122b, 122c which light when the detected gas concentration is between the high and low gas TLV thus indicating fair or poor air quality, and a red LED 122d, which lights when the detected gas concentration is above the predetermined gas TLV, thus indicating an unacceptable or dangerous concentration of gases. The circuit as generally shown in FIG. 3 is also employed in the detector instrument 100 of this embodiment and automatically assumes a low-sensitivity mode when the gas and particulates levels as detected are below their respective threshold limit values or TLVs. In the low sensitivity mode, as mentioned previously, the sampling of the particulate, gas, humidity, and temperature sensors is carried out at a low sampling rate. This permits the instrument 100 to operate at a low power drain. However, if the particulate level or the gas concentration level moves into a fair, poor, or unacceptable level, and this is sustained for more than some predetermined number of time samples, the control circuit 44 will automatically assume a high-sensitivity mode, wherein the sampling of the sensors is carried out in an increased frequency.

In the low-sensitivity mode the green indicating LED's 120a and 122a are lit, showing a good condition for both gas concentrations and particulate concentrations. This condition allows the instrument to operate in a low power draw. An audible alarm can be included to indicate a dangerous level of particulate or gas concentration.

The instrument 100 of FIG. 4 can be hand held to permit a worker to test air quality in various rooms by carrying the device from room to room. However, the same device can also be wall mounted and left within a room to indicate the air quality. In this case, a low-battery-charge indicator can also be incorporated. This feature is not shown, but many low-battery indicators are well know.

The instrument 100 can also be installed on a horizontal surface, such as a desk or table.

The gas sensor is a semi-conductor solid-state detector, utilizing tin-oxide material, although there are many other gas detectors on the market. For particulate detecting, an ionization detector or back scattering IR detector can be employed. The effects of relative humidity on particulate measurement are canceled out by the microprocessor chip.

Further, while the air conditioning and air purification unit 10 of FIG. 1 and 2 has selectable set points for the particulates, gas, relative humidity, and temperature levels, it should be understood that any or all of these parameters could be factory preset. The unit 10 could be constructed without the air conditioning capability, and would still fall within the main principles of the present invention.

While this invention has been described in detail with reference to certain preferred embodiments, it should be understood that the invention is not limited to those precise embodiments; rather, many modifications and variations would present themselves to those of skill in the art without departing from the scope and spirit of this invention, as defined in the appended claims.

What is claimed is:

1. A portable electronic device for sensing and indicating air quality within a given environmental air space, comprising a housing; particulate sensor means in said housing for detecting ambient concentration of aerosol and particulate in the space and comparing same with a predetermined particulate threshold limit value and providing a particulate sensor output; gas sensor means in said housing for detecting ambient concentration of a predetermined gas and comparing same with a gas concentration threshold limit value and providing a gas sensor output; temperature sensor means in said housing for sensing ambient temperature in said space in the vicinity of said device and providing a temperature output; humidity sensor means in said housing for detecting ambient relative humidity in said space in the vicinity of said device and providing a relative humidity output; particulate display means on an outer panel of said housing for providing a "good" indication when the ambient concentration level of particulates detected by said particulate sensor means is below said threshold limit value but providing an unsatisfactory indication when the detected ambient concentration is above said threshold limit value; gas concentration display means on an outer panel of said housing for providing a "good" indication when the detected ambient concentration of said predetermined gas is below said gas concentration threshold limit value, but providing an unsatisfactory indication when said detected ambient concentration is above said gas concentration threshold limit value; temperature display means on an outer panel of said housing for providing a display of the ambient temperature sensed by said temperature sensor means; humidity display means on an outer panel of said housing for providing a display of the ambient relative humidity detected by said humidity sensor means; and microprocessor means contained within said housing and having inputs respectively coupled to receive at least said particulate sensor output and said gas sensor output and outputs respectively connected to said particulate display means and said gas concentration display means, said microprocessor means assuming a low-power standby mode in which said gas and particulate sensor means are sampled at a relatively low rate when said particulate sensor means and said gas sensor means detect said ambient concentrations below said particulate threshold limit value and said gas value concentration threshold limit value respectively, but automatically assuming a high sensitivity mode in which said gas and particulate sensor means are sampled at a relatively high rate when either said detected particulate level is above said particulate threshold limit value or said detected gas concentration is above said gas concentration threshold limit value.

2. The device of claim 1 wherein said particulate display means provide a unsatisfactory indication, a plurality of sub-satisfactory indications, including a "bad" indication and at least one intermediate indication.

3. The device of claim 2 wherein said particulate display means includes a plurality of LEDs including a green LED to illuminate as a "good" indication, a red LED to illuminate as said "bad" indication, and a yellow LED to illuminate as said intermediate indication.

4. The device of claim 1 wherein said gas concentration display means provides as said unsatisfactory indication a plurality of sub-satisfactory indications including a "bad" indication and at least one intermediate indication.

5. The device of claim 4 wherein said gas concentration display means includes a plurality of LEDs including a green LED to illuminate as said "good" indication, a red LED to illuminate as said "bad" indication, and a yellow LED to illuminate as said intermediate indication.

6. The device of claim 1 further comprising an alarm device coupled to said microprocessor means, the latter being operative to sound said alarm device when the detected concentration of one or more said aerosols and particulate or said gases exceeds the respective threshold limit value.

7. The device of claim 6 wherein said microprocessor means is operative to assume said high sensitivity mode and repeatedly sample said particulate sensor means and said gas sensor means and verify that the respective threshold limit value is exceeded for a predetermined number of samples before actuating said alarm device.

* * * * *